（12）United States Patent
Copland et al.

(10) Patent No.: US 7,967,440 B1
(45) Date of Patent: Jun. 28, 2011

(54) SYSTEM AND METHOD FOR CHARACTERIZING CORNEAL SURFACES

(75) Inventors: James Copland, Albuquerque, NM (US); Daniel R. Neal, Tijeras, NM (US); Thomas D. Raymond, Edgewood, NM (US); Stephen W. Farrer, Albuquerque, NM (US); Paul Pulaski, Albuquerque, NM (US)

(73) Assignee: AMO Wavefront Sciences LLC., Santa Ana, CA (US)

( * ) Notice: Subject to any disclaimer, the term of this patent is extended or adjusted under 35 U.S.C. 154(b) by 0 days.

(21) Appl. No.: 12/693,106

(22) Filed: Jan. 25, 2010

(51) Int. Cl.
*A61B 3/10* (2006.01)
(52) U.S. Cl. ......... 351/212; 351/205; 351/215; 351/221
(58) Field of Classification Search .................. 351/205, 351/210, 212, 213, 214, 215, 221, 246, 247
See application file for complete search history.

(56) References Cited

U.S. PATENT DOCUMENTS

| 5,054,907 | A | 10/1991 | Sklar et al. |
| 7,708,408 | B1 * | 5/2010 | Bor ............................... 351/212 |
| 2008/0151191 | A1 * | 6/2008 | McBeth ........................ 351/212 |
| 2009/0002361 | A1 | 1/2009 | Dote et al. |

FOREIGN PATENT DOCUMENTS

| DE | 102008008732 A1 | 8/2009 |
| EP | 0832597 A1 | 4/1998 |

* cited by examiner

*Primary Examiner* — Huy K Mai

(57) ABSTRACT

A system includes a light pattern generator having light spots for illuminating front and back surfaces of a cornea with polarized light; one or more detectors for receiving one or more of first spot images from light reflected off the front surface, and second spot images from light reflected off the back surface, the light reflected off the front surface having a first polarization and the light reflected off the back surface having a second polarization; a polarization element in an optical path between the back surface and the one or more detectors, the polarization element being configured to attenuate an intensity of the light reflected off the front surface by an amount greater than an amount by which it attenuates the light reflected off the back surface; and a processor for determining a geometric characteristic of the cornea using at least the second plurality of spot images.

20 Claims, 4 Drawing Sheets

SYSTEM AND METHOD FOR CHARACTERIZING CORNEAL SURFACES

BACKGROUND AND SUMMARY

1. Field

This invention pertains to the field of vision diagnostics, and in particular to a method and apparatus for characterizing conical shape and/or structure.

2. Description

There are a number of situations where it is desirable or necessary to determine the thickness of the cornea of an eye, or the shape of its back surface. For example, in the case that a LASIK procedure is being considered, determination of corneal thickness may be used to aid treatment planning.

There are a few non-contact methods of measuring corneal thickness. These include optical coherence topography and Scheimpflug photography.

However, it would be desirable to provide alternative systems that can characterize a back surface of a corneal and/or measure corneal thickness. It would also be desirable to provide a method of characterizing a back surface of a cornea and/or measure corneal thickness.

In one aspect of the invention, a system comprises: a light pattern generator comprising a plurality of light spots configured to illuminate a front surface and a back surface of a cornea of an eye with polarized light; one or more detectors positioned to receive one or more of a first plurality of spot images from light reflected off the front surface of the cornea, and a second plurality of spot images from light reflected off the back surface of the cornea, the light reflected off the front surface of the cornea having a first polarization and the light reflected off the back surface of the cornea having a second polarization different from the first polarization; a polarization element disposed in an optical path between the back surface of the cornea of the eye and the one or more detectors, the polarization element being configured to attenuate an intensity of the light reflected off the front surface of the cornea by an amount greater than an amount by which it attenuates the light reflected off the back surface of the cornea; and a processor configured to determine a geometric characteristic of the cornea of the eye using at least the second plurality of spot images received by the one or more detectors.

In another aspect of the invention, a method comprises: illuminating a front surface and a back surface of a cornea of an eye with polarized light from a light pattern generator comprising a plurality of light spots; directing light reflected off the front surface of the cornea and light reflected off the back surface of the cornea to a polarization element, the polarization element being configured to attenuate an intensity of the light reflected off the front surface of the cornea by an amount greater than an amount by which it attenuates the light reflected off the back surface of the cornea; receiving at one or more detectors one or more of a first plurality of spot images from light reflected off the front surface of the cornea, and a second plurality of spot images from light reflected off the back surface of the cornea, the light reflected off the front surface of the cornea having a first polarization and the light reflected off the back surface of the cornea having a second polarization different from the first polarization; and determining a geometric characteristic of the cornea of the eye using at least the second plurality of spot images received by the one or more detectors.

DETAILED DESCRIPTION

Figure 1:
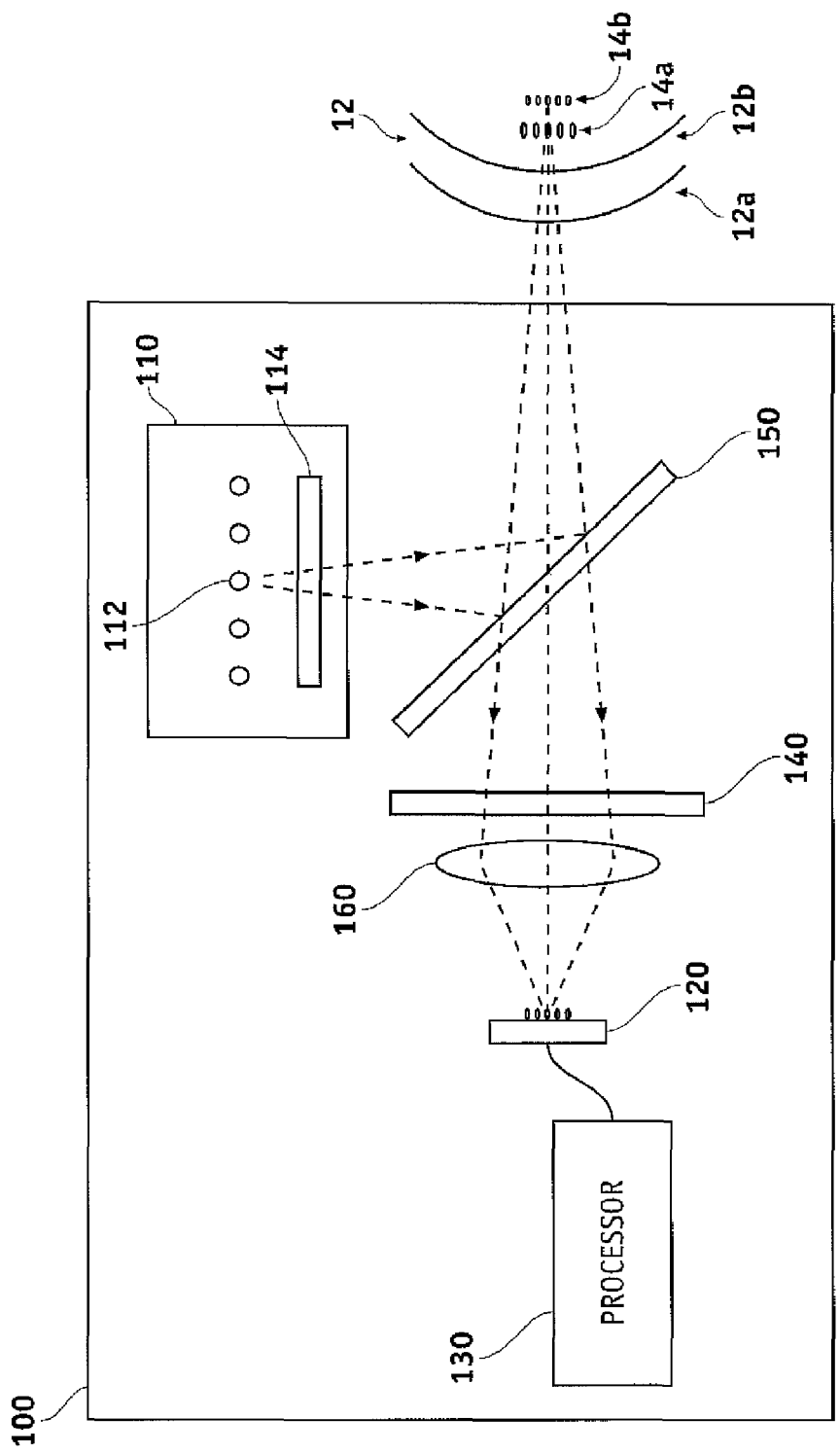
FIG. 1 illustrates one embodiment of a system for characterizing a cornea of an eye.

FIG. 1 illustrates one embodiment of a system 100 for characterizing a cornea 12 of an eye 10. System 100 comprises a light pattern generator 110, a detector 120, a processor 130, a polarization element 140, a beamsplitter 150, and a lens 160.

Light pattern generator 110 includes a plurality of light spots 112 and a polarizer 114. Light spots 112 may comprise, for example, a plurality of light-emitting diodes (LEDs). In one beneficial embodiment, light spots 112 may be arranged in the pattern of a ring. In another beneficial embodiment, light spots 112 may be arranged to lie on the surface of a cone, for example using a corneal topographer as described by Charles E. Campbell, et al., in U.S. Patent Application Publication 2009/0002361, the entirety of which is hereby incorporated by reference for all purposes as if fully set forth herein.

Beneficially, detector 120 is a detector array. Detector 120 may be a camera or charge-coupled device (CCD) array or other image-detecting device, beneficially having a plurality of pixels.

Processor 130 may be a microprocessor executing machine-readable instructions of a software program, a digital signal processor, an application specific circuit (ASIC), or any other convenient arrangement of hardware, firmware, and/or software. Beneficially, processor 130 includes memory for storing data output by detector 120, for storing executable code, for storing intermediate and final processing results of processor 130, etc.

In some embodiments, polarization element 140 may be a variable polarizing filter whose polarization can be changed. In various embodiments, polarization element 140 may include a polarizer (e.g., a linear polarizer) which can be rotated mechanically and/or under processor control to change the direction of its polarization. In other embodiments, polarization element 140 may include a spatial light modulator (e.g., a liquid crystal panel). In still other embodiments, polarization element 140 may include one or more retarding wave plates.

In system 100, beneficially beamsplitter 150 may be a non-polarizing beamsplitter.

Operationally, light spots 112 generate a pattern of light spots. Polarizer 114 applies a first polarization to the pattern of light spots. For example, the first polarization may be a linear polarization, such as a horizontal polarization or vertical polarization. Light from the polarized pattern of light spots is reflected off beamsplitter 150 and illuminates to cornea 12.

As shown in FIG. 1, the anterior surface of cornea 12, disposed toward the exterior of eye 12 is herein referred to as the "front surface" 12a of cornea 12, and the posterior surface of cornea 12, disposed toward the interior of eye 12 closest to the retina is herein referred to as the "back surface" 12b of cornea 12.

A first portion of the light from beamsplitter 150 reflects off front surface 12a of cornea, creating first images 14a of the light spots. A second portion of the light from beamsplitter 150 passes through front surface 12a into cornea 12 and reaches back surface 12b of cornea 12. A portion of the light then reflects off back surface 12b of cornea, creating second images 14b of the light spots.

The reflected light from front surface 12a and the reflected light from back surface 12b passes through beamsplitter 150 to polarization element 140.

The reflected light from front surface 12a of cornea generally retains the first polarization provided by polarizer 114. However, the light that passes through cornea 12 to reach back surface 12b has its polarization rotated or otherwise altered as it passes through the cornea, for example, because the cornea is birefringent. The polarization of the light reflected from back surface 12b and passed back through front surface 12a is changed further by the cornea. So the light from front surface 12a of cornea 12 at polarization element 140 will have the first polarization, while the light from the back surface 12b of cornea 12 at polarization element 140 will have a second polarization that is different from the first polarization. The second polarization can be represented as having a first component aligned with the first polarization and a second component orthogonal to the first polarization.

In certain embodiments, light reflected by front surface 12a is much brighter or has a higher intensity than light reflected by back surface 12b. However, if the polarization direction of polarization element 140 is cross-aligned with, orthogonal to, or nearly orthogonal to, the first polarization direction provided by polarizer 114, then polarization element 140 will attenuate or reject the reflected light from front surface 12a of cornea 12 and reduce or block light from the first images 14a from being received by detector 120. Meanwhile, most, or at least a portion, of the reflected light from back surface 12b of cornea 12 and second images 14b of the light spots is received by detector 120 to form a secondary image on detector 120. In this way, detector 120 receives images 14b of the light spots from back surface 12b of cornea 12, while light from images 14a of the light spots from front surface 12a is either attenuated or eliminated. In either case, the ratio of the brightness or intensity of images 14b to the brightness or intensity of images 14a is increased. In this way, image data at detector 120 may be used by processor 130 characterize the back surface 12b of cornea 12, characterize the front surface 12a of cornea 12, and/or characterize the cornea 12 thickness at a plurality of locations as described in greater detail below.

In some instances, the signal on detector 120 from image 14a of light reflected from front surface 12a is not completely eliminated or attenuated by a desired amount. In such instances, one or more spots from each of images 14a and 14b at least partially overlap due to their close proximity to one another, thus making it more difficult to determine a sufficiently precise location on detector 120 of the spots in image 14b of light reflected from the back surface 12b. In certain embodiments, the accuracy in determining the location of the spots in image 14b may be increased by recording or capturing a plurality of images on detector 120 of images 14a and 14b, wherein each image in the plurality is captured with polarization element 140 oriented at different polarization angles (e.g., at two or more of the angles of 90 degrees, 85 degrees, 80 degrees, 70 degrees, 60 degrees, and 50 degrees with respect to the first polarization direction provided by polarizer 114). Image processing routines (e.g., used by processor 130) may then be used to calculate centroids locations for overlapping pairs of spots from images 14a and 14b for each image recorded by detector 120 at differing polarization angles of polarization element 140. For each set of recorded spot pairs, the centroid will be different, due to a relative change of intensity between the two spots in each spot pair. By comparing the change in centroid location for a spot pair in the various recorded images, a more accurate calculation may be obtained of the location of the spot corresponding to light reflected from the back surface 12b contained in image 14b.

As noted above, in some embodiments, polarization element 140 may be a variable polarizing filter whose direction or polarization can be changed, allowing characterization of one or both surfaces 12a, 12b. When it is desired to characterize front surface 12a of cornea 12, the polarization direction of polarization element 140 may be changed to be aligned with the first polarization direction provided by polarizer 114. Then, polarization element 140 will pass the reflected light from front surface 12a of cornea 12 and allow first images 14a of the light spots from front surface 12a to be formed on detector 120. Polarization element 140 will also pass a portion of the reflected light from back surface 12b of cornea 12 to detector 120. However, the images 14a will appear much brighter on detector 120 than the images 14b. From this image data, processor 130 can characterize the front surface 12a of cornea 12.

In some embodiments, a measure of the thickness of cornea 12 can be obtained from the above-described data for the front surface 12a and back surface 12b of cornea 12, as will be described in greater detail below.

Figure 2:
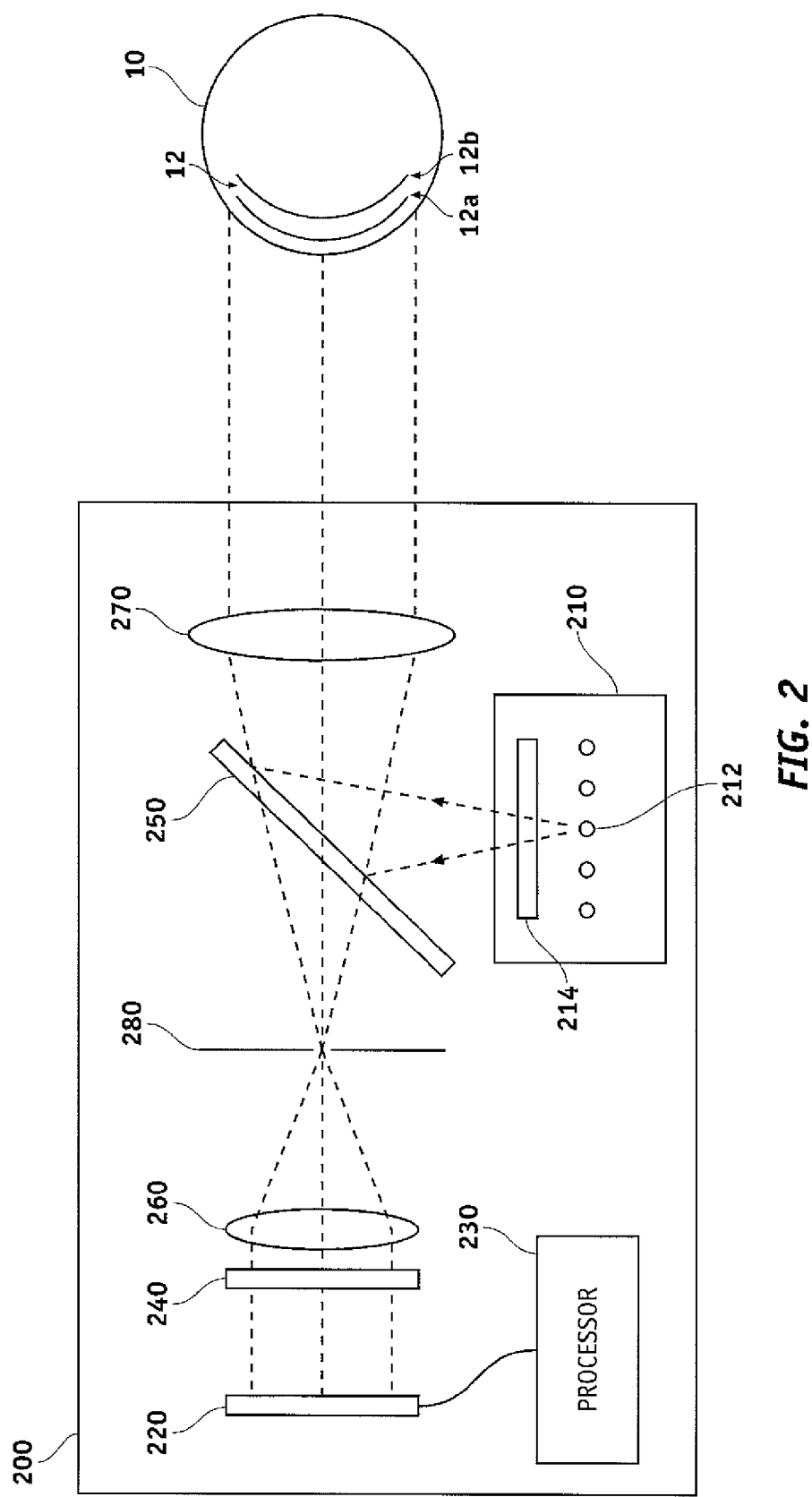
FIG. 2 illustrates another embodiment of a system for characterizing a cornea of an eye.

FIG. 2 illustrates one embodiment of a system 200 for characterizing a cornea 12 of an eye 10. System 200 comprises a light pattern generator 210, a detector 220, a processor 230, a polarization element 240, a beamsplitter 250, a first lens 260, a second lens 270, and an optional aperture 280 that filters stray light from reaching detector 220.

Light pattern generator 210 includes a plurality of light spots 212 and a polarizer 214. Although only a single light spot 212 is shown in FIG. 2 for simplification, it should be understood that a plurality of such sources are present. In one beneficial embodiment, light spots 212 may be arranged in the pattern of a ring. In another beneficial embodiment, light spots 212 may be arranged to lay on the surface of a cone, for example using a corneal topographer as described by Charles E. Campbell, et al., in U.S. Patent Application Publication 2009/0002361.

Beneficially, detector 220 is a detector array. Detector 220 may be a camera or charge-coupled device (CCD) array or other image-detecting device, beneficially having a plurality of pixels.

Processor 230 may be a microprocessor executing machine-readable instructions of a software program, a digital signal processor, an application specific circuit (ASIC), or any other convenient arrangement of hardware, firmware, and/or software. Beneficially, processor 230 includes memory for storing data output by detector 220, for storing executable code, for storing intermediate and final processing results of processor 230, etc.

In some embodiments, polarization element 240 may be a variable polarizing filter whose polarization can be changed. In various embodiments, polarization element 240 may include a polarizer (e.g., a linear polarizer) which can be rotated mechanically and/or under processor control to change the direction of its polarization. In other embodiments, polarization element 240 may include a spatial light modulator (e.g., a liquid crystal panel). In still other embodiments, polarization element 240 may include one or more retarding wave plates.

In system 200, beamsplitter 250 may be a non-polarizing beamsplitter.

System 200 is similar to that of system 100, except for the optional aperture 280, discussed above, and second lens 270. Second lens collimates the polarized light from each of the light spots 212 of light pattern generator 210 and provides the collimated, polarized light to cornea 12 (for simplicity and clarity, FIG. 2 only traces the light rays from one light spot 212). Accordingly, system 200 is said to include a plurality of Helmholtz sources. The operation of system 200 is similar to that of system 100 described in detail above, and so a detailed description of that operation will be omitted in the interest of brevity.

The examples above employed a single detector and a single illumination wavelength. Additional information could be obtained by using a combination of illuminating wavelengths multiple detectors. Such detectors could be co-aligned or aligned at different angles.

Figure 3:
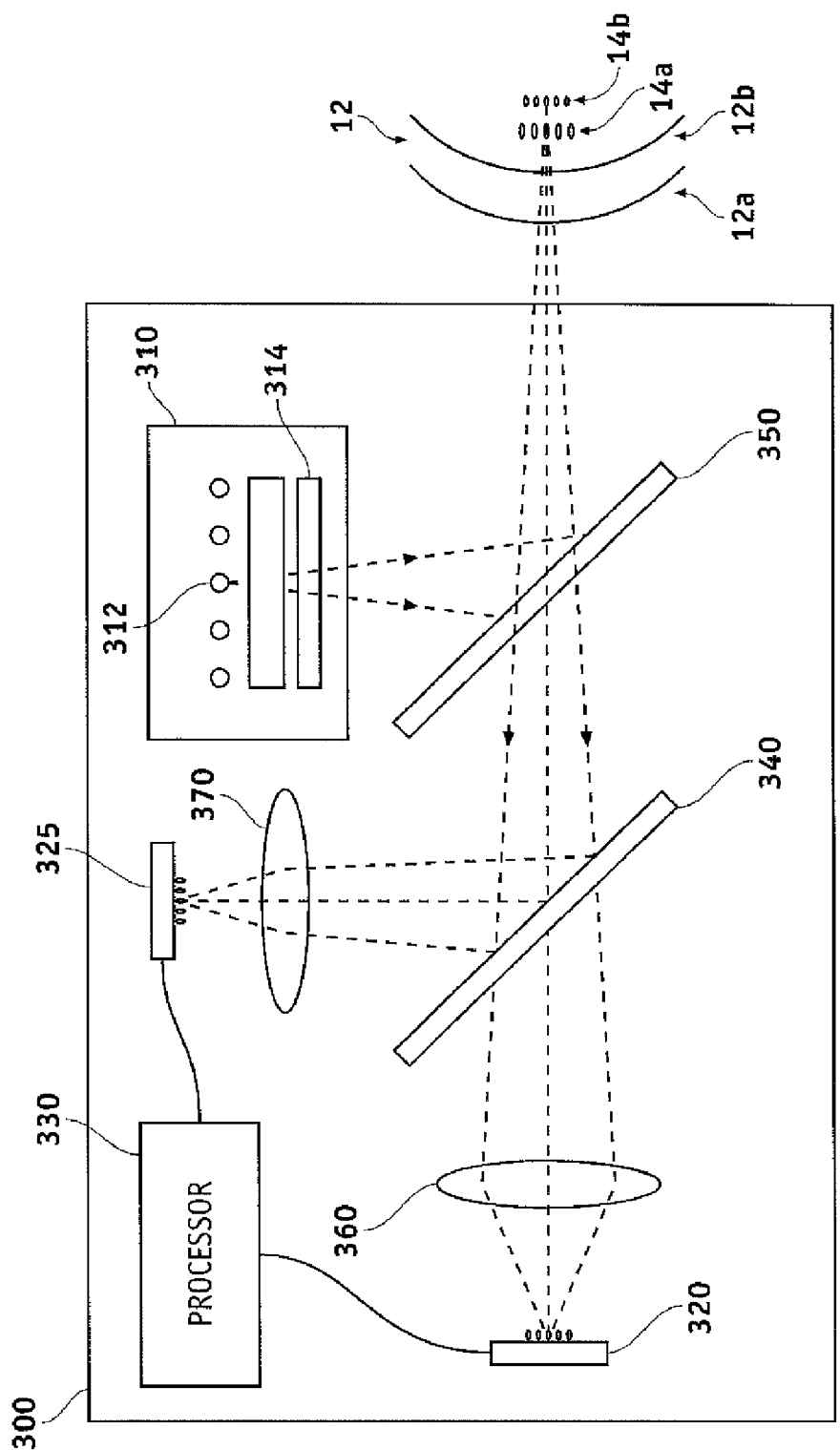
FIG. 3 illustrates yet another embodiment of a system for characterizing a cornea of an eye.

FIG. 3 illustrates another embodiment of a system 300 for characterizing a cornea 12 of an eye 10. System 300 comprises a light pattern generator 310, a first detector 320, a second detector 325, a processor 330, a polarization element comprising polarizing beamsplitter 340, a non-polarizing beamsplitter 350, a first lens 360 and a second lens 370.

Light pattern generator 310 includes a plurality of light sources 312 and a polarizer 314.

Beneficially, first and second detectors 320 each comprise a detector array. Detectors 320 and 325 each may be a camera or charge-coupled device (CCD) array or other image-detecting device, beneficially having a plurality of pixels.

Processor 330 may be a microprocessor executing machine-readable instructions of a software program, a digital signal processor, an application specific circuit (ASIC), or any other convenient arrangement of hardware, firmware, and/or software. Beneficially, processor 330 includes memory for storing data output by detectors 320 and 325, for storing executable code, for storing intermediate and final processing results of processor 330, etc.

In system 300, beamsplitter 350 may be a non-polarizing beamsplitter.

The operation of system 300 is similar to that of system 100, except for the following differences. In system 300, beamsplitter 340 is a polarized beamsplitter which directs light having the first polarization of the polarizer 314 toward a first one of the detectors 320 and 325 (e.g., first detector 320), and directs light having a polarization orthogonal to the first polarization of the polarizer 314 toward the other one of the detectors 320 and 325 (e.g., second detector 325). Alternatively, in some embodiments polarizing beamsplitter 340 may be replaced by a non-polarizing beamsplitter, in which case one or more additional polarization elements are disposed between the non-polarizing beamsplitter and detectors 320 and/or 325.

In some embodiments, light from images 14a of the light spots from front surface 12a is attenuated or eliminated so that second detector 325 receives image 14b of the light spots from back surface 12b of cornea 12 without interference, or with reduced interference, from the light reflected from front surface 12a. Meanwhile, first detector 320 receives first images 14a of the light spots from front surface 12a or cornea 12. Beamsplitter 340 may also pass a portion of the reflected light from back surface 12b of cornea 12 to detector 320. However, the images 14a will generally appear much brighter on detector 320 than the images 14b. From the image data, processor 330 can characterize the cornea 12.

The cornea is known to have a nominal pattern of birefringence, with a slow axis pointed downward and nasally. This will tend to make the pattern of spots seen by the detector confusing. In some embodiments a polarization element (e.g., an LCD panel) may be programmed with a spatial polarization pattern to compensate for the birefringence pattern of the cornea. In some embodiments, this pattern may be fixed. In some embodiments, this pattern may be adapted to each eye as it is measured.

In addition to reflections off the front and back surfaces of the cornea, there can be reflections that involve light reflecting from the interior of the cornea that create images similar to the images produced by the front and back surfaces of the cornea. In some embodiments, these images can also be analyzed to determine information for characterizing the cornea, such as corneal thickness.

Also, in some embodiments, to assist in determining which images are produced from which surfaces, in some embodiments various ones of the light sources may be operated sequentially instead of simultaneously.

Figure 4:
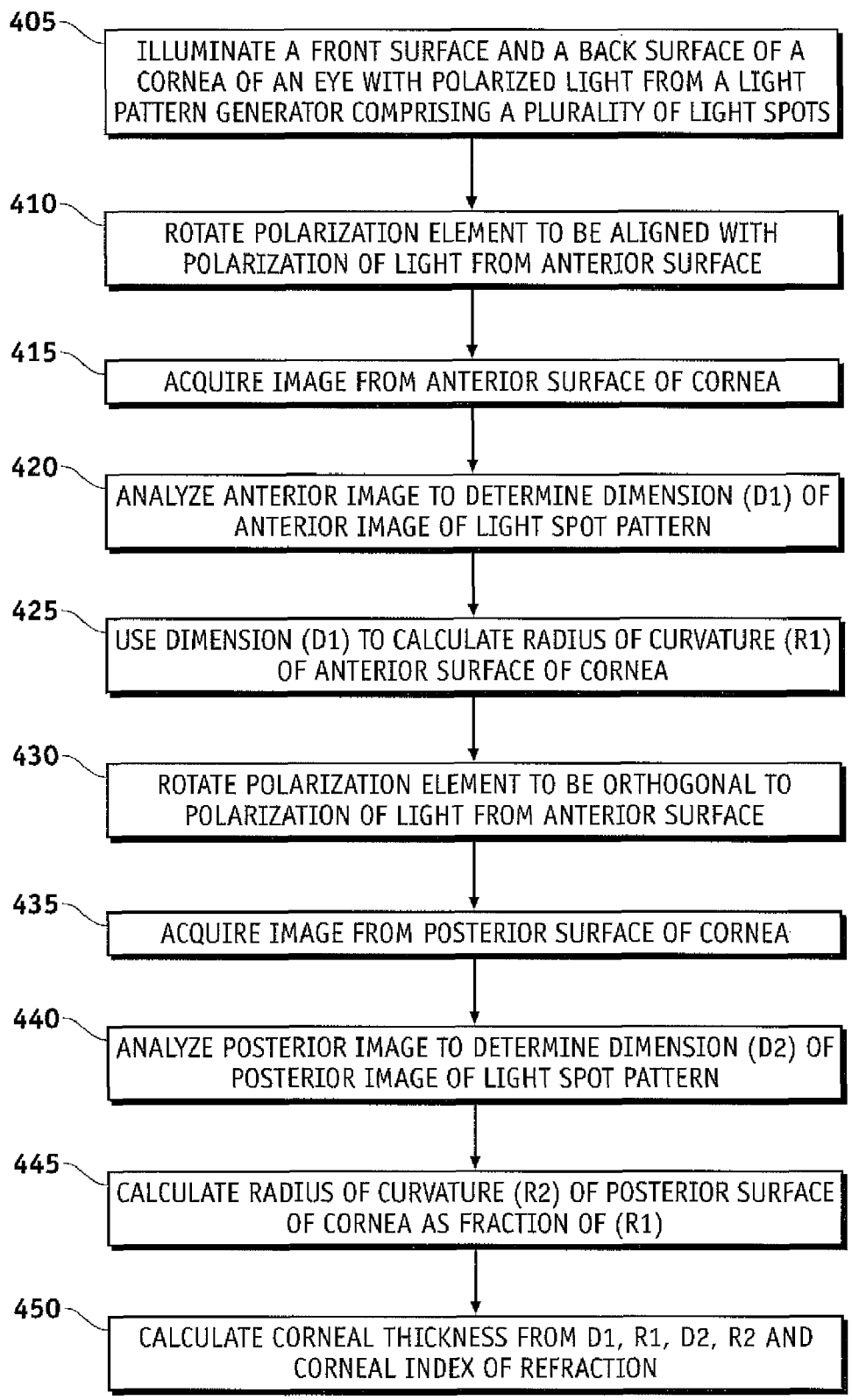
FIG. 4 illustrates one embodiment of a method of determining a geometric characteristic of a cornea of an eye.

FIG. 4 illustrates one embodiment of a method 400 of determining a geometric characteristic of a cornea of an eye.

In a first step 405, a system (e.g., a corneal topographer) illuminates a front surface and a back surface of a cornea of an eye with polarized light from a light pattern generator comprising a plurality of light spots.

In a step 410, a polarization element in the system is rotated to be aligned or substantially aligned with the polarization of light being reflected by the anterior (front) surface of the cornea.

In a step 415, a detector of the system acquires an image of the anterior (front) surface of the cornea.

In a step 420, a processor of the system analyzes the anterior corneal image to determine a dimension (D1) of the anterior image of the light spot pattern. For example, when the light spot pattern comprises a ring, then the system analyzes the anterior corneal image to determine the diameter of the anterior image of the ring.

In a step 425, the processor uses the dimension (D1) to calculate the radius of curvature (R1) of the anterior surface of the cornea, for example using conventional corneal typography analysis.

In a step 430, the polarization of the polarization element is rotated so as to be orthogonal, or substantially orthogonal, to the polarization of the light from the anterior surface of the cornea.

In a step 435, a detector of the system acquires an image of the posterior (back) surface of the cornea.

In a step 440, a processor of the system analyzes the posterior conical image to determine a dimension (D2) of the posterior image of the light spot pattern. For example, when the light spot pattern comprises a ring, then the system analyzes the posterior corneal image to determine the diameter of the posterior image of the ring In a step 445, the processor calculates the radius of curvature (R2) of the posterior surface of the cornea. In one embodiment, the processor may calculate R2 as a fraction of (R1), the radius of curvature of the anterior surface of the cornea using a known multiplication factor based on empirical data from human eye measurements. For example, in one embodiment (R2) is calculated as 0.833*(R1).

In a step 450, the processor calculates the thickness of the corneal from (R1), (R2), (D1), (D2), and an index of refraction, N, of the cornea. For example, based on empirical data from human eye measurements, N generally equals 1.376, and this value may be used together with the previously-determined values of R1), (R2), (D1), (D2) to determine the corneal thickness. In some embodiments, a ray tracing algorithm may be employed to determine the corneal thickness. In some embodiments, an empirical equation, derived from the same physics as the ray tracing algorithm, may be solved to calculate the corneal thickness.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A system, comprising:
 a light pattern generator comprising a plurality of light spots configured to illuminate a front surface and a back surface of a cornea of an eye with polarized light;
 one or more detectors positioned to receive one or more of a first plurality of spot images from light reflected off the front surface of the cornea and a second plurality of spot images from light reflected off the back surface of the cornea, the light reflected off the front surface of the cornea having a first polarization and the light reflected off the back surface of the cornea having a second polarization different from the first polarization;
 a polarization element disposed in an optical path between the back surface of the cornea of the eye and the one or more detectors, the polarization element being configured to attenuate an intensity of the light reflected off the front surface of the cornea by an amount greater than an amount by which it attenuates the light reflected off the back surface of the cornea; and
 a processor configured to determine a geometric characteristic of the cornea of the eye using at least the second plurality of spot images received by the one or more detectors.

2. The system of claim 1, wherein the geometric characteristic of the cornea comprises one or more of a radius of curvature of the back surface, a radius of curvature of the front surface, a shape of the back surface, a shape of the front surface, and a thickness between the front surface and the back surface.

3. The system of claim 1, wherein the light pattern generator further comprises a linear polarizer and the first polarization is a linear polarization produced by the linear polarizer, and the polarization element is configured to reject light having the first polarization and to pass light orthogonal to the first polarization.

4. The system of claim 1, wherein the polarization element comprises one or more of a linear polarizer, a spatial light modulator, and a retarding phase plate.

5. The system of claim 1, further comprising a beamsplitter configured to provide the polarized light from the light pattern generator to the cornea of the eye, and to provide the one or more of the first plurality of spot images from light reflected off the front surface of the cornea and the second plurality of spot images from light reflected off the back surface of the cornea to the polarization element.

6. The system of claim 1, wherein the light pattern generator comprises:
 a plurality of light sources corresponding to the light spots; and
 a polarizer for polarizing light from the plurality of light sources.

7. The system of claim 1, wherein the light spots are arranged in a ring.

8. The system of claim 1, wherein the light spots lie on a surface of a cone.

9. The system of claim 1, further comprising a collimating lens disposed in an optical path between the light pattern generator and the cornea.

10. The system of claim 1, wherein the one or more detectors includes:
 a first detector configured to receive the first plurality of spot images from the light reflected off the front surface of the cornea; and
 a second detector configured to receive the second plurality of spot images from the light reflected off the back surface of the cornea.

11. The system of claim 10, wherein the polarization element comprises a polarizing beamsplitter, the polarizing beamsplitter being configured to pass the one or more images of the one or more light spots from the back surface of the cornea of the eye to the first detector, and to pass the one or more images of the one or more light spots from the front surface of the cornea of the eye to the second detector.

12. The system of claim 1, wherein the one or more detectors comprises one detector configured to receive both the first plurality of spot images from the light reflected off the front surface of the cornea, and the second plurality of spot images from the light reflected off the back surface of the cornea.

13. A method, comprising:
 illuminating a front surface and a back surface of a cornea of an eye with polarized light from a light pattern generator comprising a plurality of light spots;
 directing light reflected off the front surface of the cornea and light reflected off the back surface of the cornea to a polarization element, the polarization element being configured to attenuate an intensity of the light reflected off the front surface of the cornea by an amount greater than an amount by which it attenuates the light reflected off the back surface of the cornea;
 receiving at one or more detectors one or more of a first plurality of spot images from light reflected off the front surface of the cornea and a second plurality of spot images from light reflected off the back surface of the cornea, the light reflected off the front surface of the cornea having a first polarization and the light reflected off the back surface of the cornea having a second polarization different from the first polarization; and
 determining a geometric characteristic of the cornea of the eye using at least the second plurality of spot images received by the one or more detectors.

14. The method of claim 13, wherein the geometric characteristic of the cornea comprises one or more of a radius of curvature of the back surface of the cornea, a radius of curvature of the front surface of the cornea, a shape of the back surface, a shape of the front surface, and a thickness between the front surface and the back surface.

15. The method of claim 13, wherein the polarization element comprises one or more of a spatial light modulator array, a retarding phase plate, and a linear polarizer.

16. The method of claim 13, wherein illuminating the front surface and the back surface of the cornea further comprises passing the polarized light spots through a collimating lens disposed in an optical path between the light pattern generator and the cornea.

17. The method of claim 13, wherein the light spots are arranged in a ring.

18. The method of claim 13, wherein the light spots lie on a surface of a cone.

19. The method of claim 13, wherein receiving at one or more detectors comprises receiving at a single detector both the first plurality of spot images from light reflected off the front surface of the cornea and the second plurality of spot images from light reflected off the back surface of the cornea.

20. The method of claim 13, wherein receiving at one or more detectors comprises receiving at a first detector the first plurality of spot images from the light reflected off the front surface of the cornea and receiving at a second detector the second plurality of spot images from light reflected off the back surface of the cornea.

* * * * *